United States Patent [19]

Sartori

[11] Patent Number: 4,618,721
[45] Date of Patent: Oct. 21, 1986

[54] PROCESS FOR THE PREPARATION OF NITRODIPHENYL DISULFIDES

[75] Inventor: Vittore Sartori, Riehen, Switzerland
[73] Assignee: Ciba-Geigy Corporation, Ardsley, N.Y.
[21] Appl. No.: 714,308
[22] Filed: Mar. 21, 1985
[30] Foreign Application Priority Data Mar. 26, 1984 [CH] Switzerland .......................... 1499/84

[51] Int. Cl.$^4$ ........................................... C07C 148/00
[52] U.S. Cl. .................................. 568/23; 260/505 R
[58] Field of Search ........................ 568/23; 260/505 R

[56] References Cited

U.S. PATENT DOCUMENTS 3,784,534  1/1974  Yosioka et al. ........................ 508/23

FOREIGN PATENT DOCUMENTS 3216126  11/1983  Fed. Rep. of Germany .
1222768  2/1971  United Kingdom .
1325972  8/1973  United Kingdom .

OTHER PUBLICATIONS

Methoden der Organ. Chemie Houben-Weyl, Band IX, 1955, pp. 65–67.
Textile Chemicals and Auxiliaries—Speel et al—Chapter 13, pp. 301–320.
Irgasol DAM, Technical Bulletin (Circular), Dispersant for Use in Dyeing Cellulosic Fibers, Polyester and Blends Containing Polyester, Levelling Agent for Use in Dyeing Acrylic Fibers and Wool.
Irgasol P., Technical Bulletin (Circular), Dispersant To Assist Fluorescent Whitening and Dyeing of Synthetic Fibers, Fixation Accelerant for Pad-Bake Fluorescent Whitening and Pad-Thermosol Dyeing.
V. Lukashevich et al, Chem. Abstracts 44: 3451i (1949).
E. Reid, Organic Chemistry of Bivalent Sulfur, vol. III, pp. 363–365 (1960), Chemical Publishing Co., N.Y.

Organic Syntheses Coll. vol. I, pp. 220–221, H. Gilman (ed.).
Helv. Chim. Acta, pp. 663–668, (1929), H. Fierz et al.
J. Chem. Soc., pp. 1002–1004, (1948), H. Hodgson et al.
Albegal A, Technical Bulletin (Circular) Versatile Levelling Agent, Mainly Used for 1:2 Metal Complex Dyes and for Acid and Chrome Dyes, (Ciba-Geigy).
Diphasol OL, Technical Bulletin (Circular), Detergent for Use in Washing Off Prints, (Ciba-Geigy).
Invaderm AL, Färberei-Hilfsmittel, (Ciba-Geigy).

Primary Examiner—Donald G. Daus
Assistant Examiner—Mary E. Ceperley
Attorney, Agent, or Firm—Edward McC. Roberts; Kevin T. Mansfield; Irving M. Fishman

[57] ABSTRACT

The invention describes a process for the preparation of nitrodiphenyl disulfides by reacting halonitrobenzenes of the formula

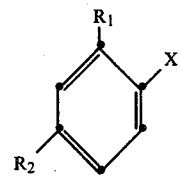

wherein X is chlorine, bromine or iodine, $R_1$ is hydrogen or nitro and $R_2$ is hydrogen, $C_1$–$C_4$ alkyl, halogen, nitro or the sulfo group, with the proviso that at least one of $R_1$ and $R_2$ is nitro, with an alkali disulfide, which process comprises carrying out the reaction in water with the addition of a non-ionic and/or anionic surfactant.

Nitrodiphenyl disulfides are important intermediates and are used, inter alia, for the manufacture of textile dyes.

10 Claims, No Drawings

PROCESS FOR THE PREPARATION OF NITRODIPHENYL DISULFIDES

The present invention relates to a process for the preparation of nitrodiphenyl disulfides by reacting halonitrobenzenes with an alkali disulfide.

Nitrodiphenyl disulfides are valuable intermediates which find utility as starting materials for the preparation of various important compounds that are manufactured on a large scale, for example nitrobenzenesulfonic acid, nitrobenzenesulfochloride and orthanilic acid.

The synthesis of nitrodiphenyl disulfides starting from halonitrobenzenes has long been known. H.E. FIERZ et al in Helv. Chim. Acta 663 (1929) describe a process for the preparation of o,o'-dinitrodiphenyl disulfide by reacting o-nitrochlorobenzene, sodium sulfide and sulfur in alcoholic solution (q.v. also Org. Synth. Coll. Vol. I, p. 220). The same reaction, but using cyclic or open-chain carboxamides such as N-methylcaprolactam as solvent, is described in DE-OS 22 04 726. Further, processes for the preparation of 2,2',4,4'-tetranitrodiphenyl disulfide are found in the literature. Reference is made in this connection to work described by H.H. HODGSON et al in J. Chem. Soc. 1002 (1948) and by V. O. LUKASHEVICH et al in Zhur. Obshchei Khim. 19, 1493 (1949) - Chem. Abstr. 44 3451i (1950). The reaction medium employed by these authors is alcohol or a mixture of alcohol and water. The yields obtained by these known prior art processes are reported to be from 68 to 86% of theory and are thus of an order of magnitude that is unsatisfactory for intermediates manufactured on a large scale. A secondary reaction that contributes to the diminution of yield is, in particular, the reaction of the nitro groups both in the final product and in the starting materials. Only in the reaction described in DE-OS No. 22 04 726 and carried out in carboxamides are yields of 94 % of theory achieved. However, the solvents employed in this process are relatively expensive and have to be regenerated at the conclusion of the synthesis.

Hence it is the object of the present invention to provide a process for the preparation of nitrodiphenyl disulfides that affords a yield of over 90% and which does not require the use of solvents that are troublesome to purify.

This object is achieved by using water as reaction medium and emulsifying the starting compound, namely the water-insoluble halonitrobenzene, with the aid of a surfactant. In spite of the heterogeneous system, it is found that the reaction proceeds so as to give a surprisingly high yield.

Accordingly, the present invention relates to a process for the preparation of nitrodiphenyl disulfides by reacting halonitrobenzenes of the formula

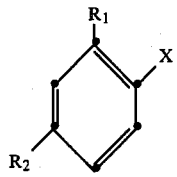

with an alkali disulfide, which process comprises carrying out the reaction in water with the addition of an anionic and/or non-ionic surfactant. The symbols indicated in the formula above are defined as follows: X is a chlorine, bromine or iodine atom, $R_1$ is hydrogen or the nitro group and $R_2$ is hydrogen, $C_1$–$C_4$alkyl, halogen, the nitro or sulfo group, with the proviso that at least one of $R_1$ and $R_2$ is the nitro group. By halogen is meant fluorine, chlorine, bromine or iodine. Suitable $C_1$–$C_4$alkyl radicals are for example methyl, ethyl, propyl, isopropyl or butyl.

The reaction proceeds in accordance with the following equation:

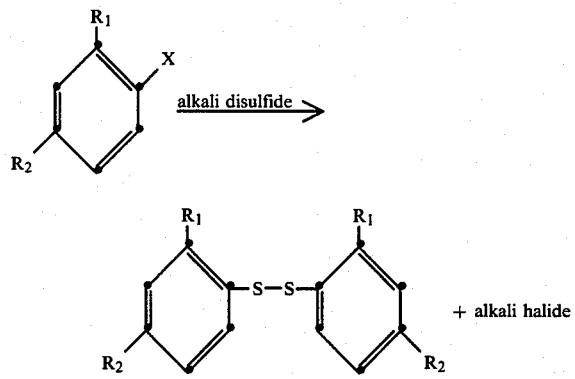

Halonitrobenzenes which are reacted to the corresponding nitrodiphenyl disulfides in the process of this invention are, in particular, 1-bromo-2-nitrobenzene, 1-chloro-4-nitrobenzene, 1-bromo-4-nitrobenzene, 1-chloro-2,4-dinitrobenzene, 1-bromo-2,4-dinitrobenzene and, most particularly, 1-chloro-2-nitrobenzene.

The individual halonitrobenzenes are known. They are obtained, for example, by the nitration of halobenzenes [Houben-Weyl; Methoden der organischen Chemie, Vol. 10/1, pp. 499–515 (1971)].

The alkali disulfide is conveniently freshly prepared, before the reaction, from alkali hydrogen sulfide and sulfur in alkaline solution. But it can also be prepared in situ in known manner from an alkali sulfide and sulfur. It is preferred to use sodium disulfide. The alkali disulfide is conveniently employed in small excess, i.e. about 0.55 to 0.6 mole of alkali disulfide is used per 1 mole of halonitrobenzene.

The surfactants employed for emulsifying the halonitrobenzenes are non-ionic and anionic surfactants which may belong to a very wide range of compound classes.

Non-ionic surfactants are preferably adducts of ethylene oxide and alkylphenols, fatty alcohols, fatty amines or fatty acids (ethoxylates). The molecular weight of these adducts is in the range from 300 to 10,000.

Preferred ethylene oxide adducts are:

(a) adducts of saturated and/or unsaturated $C_{10}$–$C_{20}$fatty alcohols and 5 to 40 moles of ethylene oxide per mole of fatty alcohol;

(b) adducts of $C_4$–$C_{12}$alkylphenols and 5 to 40 moles, preferably 5 to 20 moles of ethylene oxide per mole of alkylphenol;

(c) adducts of saturated and/or unsaturated $C_{14}$–$C_{25}$fatty amines and 10 to 40 moles of ethylene oxide per mole of fatty amine;

(d) adducts of saturated and/or unsaturated $C_{14}$–$C_{20}$fatty acids and 5 to 40 moles of ethylene oxide per mole of fatty acid.

The preferred ethylene oxide adducts are those mentioned in (d), viz. those having a molecular weight of 500 to 1500.

It is also possible to use mixtures of the ethylene adducts of (a), (b), (c) and (d) with one another. These mixtures are obtained by mixing individual adducts or direct by ethoxylating a mixture of the compounds from which they are derived. It will be understood that mixtures of ethylene oxide adducts within a group are also possible, for example those obtained by ethoxylating a mixture of fatty alcohols of different chain length.

Suitable saturated and/or unsaturated fatty alcohols in (a) are dodecanol, palmityl alcohol, cetyl alcohol, stearyl alcohol, oleyl alcohol or tallow fatty alcohols, preferably a mixture of $C_{12}$–$C_{19}$ fatty alcohols, for example a mixture of cetyl alcohol and stearyl alcohol.

The alkylphenols in (b) are butylphenol, hexylphenol, and preferably isooctylphenol, p-tert-octylphenol, nonylphenol and dodecylphenol.

In addition to stearylamine, palmitylamine and oleylamine, a suitable fatty amine in (c) is in particular a mixture of $C_{18}$–$C_{22}$ fatty amines.

Examples of saturated and/or unsaturated fatty acids in (d) are, in particular, stearic acid, ricinoleic acid and oleic acid.

The anionic surfactants are in particular condensates of formaldehyde and aromatic sulfonic acids, alkylbenzimidazoledisulfonic acids containing 10 to 25 carbon atoms in the alkyl moiety, and also alkylphenol polyglycol ether sulfates or phosphates containing 5 to 15 carbon atoms in the alkyl moiety, or $C_6$–$C_{20}$ alkylbenzenesulfonates.

Fatty alcohol glycol ether sulfates as well as sulfonated or sulfated dicarboxylic acid esters also have good emulsifying properties in the process of this invention.

The anionic surfactants are normally in the form of their alkali metal salts, of their ammonium salts, or of their water-soluble amine salts.

It will be appreciated that mixtures of non-ionic and anionic surfactants can also be used for emulsifying the halonitrobenzenes, in particular mixtures of an adduct of a saturated and/or unsaturated $C_{14}$–$C_{20}$ fatty acid and 5 to 40 moles of ethylene oxide, based on 1 mole of fatty acid, and a $C_6$–$C_{20}$ alkylbenzenesulfonate.

The surfactant is conveniently employed in a concentration of 2 to 30% by weight, preferably of 5 to 10% by weight, based on halonitrobenzene.

The water employed as reaction medium is required only in an amount corresponding to about that of the halonitrobenzene. In particular, at the start of the reaction an even smaller amount of water of 40 to 70% by weight, based on the amount of halonitrobenzene, suffices. This concentrated mode of operation—an essential feature of the present invention—affords a high space-time yield.

The reaction is conveniently carried out in the temperature range from 40° to 100° C. Decisive for the choice of reaction temperature is, inter alia, the melting point of the respective halonitrobenzene to be reacted.

The procedure for carrying out the process of the invention is conveniently such that the halonitrobenzene is first emulsified with the surfactant in the appropriate amount of water, and the requisite amount of alkali disulfide is added to this emulsion. In order to prevent as far as possible the formation of by-products, it is advantageous to add the solution of the alkali disulfide slowly in portions or continuously over a substantial period of time. The rate of addition can be controlled via the redox potential and a constant concentration of disulfide can thus be achieved over the entire duration of the reaction.

A further possibility consists in charging the water, together with the surfactant and, optionally, a portion of the educt to the reaction vessel and then synchronously adding the halonitrobenzene on the one hand and the aqueous disulfide solution on the other.

Irrespective of the mode of carrying out the process, an almost complete conversion of the starting compound to the disulfide is achieved in particular when both the educt and the product are continuously dispersed in the reaction medium during the reaction. In this manner the formation of agglomerates of nitrodipohenyl disulfide and unreacted educt is largely avoided. In this connection it is useful to fit the reaction vessel with baffles or with a dismembrator or to apply ultrasonics.

The nitrodiphenyl disulfide is obtained at the conclusion of the reaction in the form of fine crystals and can be readily isolated by filtration or also centrifuged off. The isolated product is preferably washed with water.

The process of this invention can be carried out for example as follows:

With efficient stirring, 1-chloro-2-nitrobenzene is emulsified in water at about 60° C. with the aid of a non-ionic surfactant, e.g. a fatty acid ethoxylate. An aqueous solution of sodium disulfide is then pumped to the reaction vessel continuously over several hours, which solution has been freshly prepared beforehand from sodium hydrogen sulfide and sulfur in sodium hydroxide solution. The reaction is slightly exothermic. With cooling, the temperature is kept in the range from 55° to 70° C. The course of the reaction can be easily followed from the colour of the reaction mixture. At the start, the colour of the reaction mixture is red. In the further course of the reaction, a greenish yellow precipitate forms and the aqueous phase turns bright red. When the addition of sodium disulfide is complete, the batch is stirred briefly and then cooled to 30°–45° C. The product is isolated by filtration and washed with cold water. The yield is over 90% of theory.

Nitrodiphenyl disulfides are obtained in over 90% yield by the process of this invention. The process is easy to perform and low in cost. It affords a high space-time yield. As water is used as reaction medium, there are no solvents to be regenerated.

The invention is illustrated by the following Examples, in which parts and percentages are by weight.

EXAMPLE 1

Preparation of sodium disulfide 467 parts of sodium hydrogen sulfide as 41% solution are charged to a stirred reactor and then 334 parts of NaOH are added in the form of a 30% solution. The batch becomes gel-like and then clear again on being heated to 50° C. Then 267 parts of ground sulfur are added and stirring is continued at 65°–70° C. until a clear solution of sodium disulfide is formed.

Condensation 2500 parts of molten 1-chloro-2-nitrobenzene are charged to a stirred reactor and 150 parts of castor oil ethoxylate (about 15 moles of ethylene oxide per 1 mole of ricinoleic acid) and 1300 parts of water are added. The batch is heated to 60° C. and emulsified by efficient stirring. The freshly prepared sodium disulfide solution is then introduced beneath the surface of the emulsion.

A total amount of 2520 parts of disulfide solution is added, the rate of addition being initially about 300 parts per hour and, towards the end of the reaction, about 100 parts per hour. The ensuing reaction is slightly exothermic and by cooling the temperature is kept in a range of 60° to 65° C.. Aggregates of 2,2'-dinitrodiphenyl disulfide and 1-chloro-2-nitrobenzene formed during the reaction are comminuted with e.g. a dismembrator. Chloronitrobenzene and resultant disulfide are continuously dispersed in the reaction medium by vigorously stirring the reaction mixture. After the total amount of disulfide solution is present in the reaction vessel, stirring is continued until the reaction mass consists of individual yellow crystals and of colourless to tea-coloured mother liquor. The batch is then cooled to 40° C., and the product is isolated by filtration and washed with cold water until the washings are colourless, affording 2897 parts of 80% 2,2'-dinitrodiphenyl disulfide, corresponding to a yield of 95% of theory. Melting point: 182°-184° C. (lit.: 196° C.).

A homogeneous nitrochlorobenzene emulsion is also obtained by using one of the following surfactants instead of castor oil ethoxylate: nonylphenol ethoxylate (nonylphenol/ethylene oxide in the molar ratio of 1:9), lauryl glycol ether sulfate or also a formaldehyde/naphthalenesulfonic acid condensate, a nonylphenol ethoxylate esterified with phosphoric acid, or a sulfated maleic acid ester.

2,2'-Dinitrodiphenyl disulfide is an important dye intermediate and, after oxidative cleavage of the disulfide bridge, is used e.g. for the manufacture of acid dyes for dyeing polyamide fibre material.

EXAMPLE 2

1300 parts of water containing 150 parts of castor oil ethoxylate and 250 parts of 1-chloro-2-nitrobenzene are charged to a reactor and heated to 60° C. with thorough mixing. Simultaneous addition is then made of 2268 parts of disulfide solution (preparation as described in Example 1) and 2250 parts of 1-chloro-2-nitrobenzene in separate streams. The rate of addition is 400 parts per hour. When the total amount of chloronitrobenzene has been added, the remaining amount of disulfide is added at a rate of 100 parts per hour. The reaction is slightly exothermic and the temperature is kept in the range from 60°-65° C. by cooling. During the reaction, both the continuously added chloronitrobenzene and the resultant disulfide are continuously dispersed in the reaction mixture. This is done by constant and intensive mixing. Agglomerates are comminuted with a dismembrator. After the total amount of disulfide has been added as well, stirring is continued until the reaction mass consists of individual yellow crystals and of a colourless to tea-coloured mother liquor. The batch is then cooled to 40° C. and filtered. The product is washed with cold water until the washings are colourless, affording 2,2'-dinitrodiphenyl disulfide which contains about 5% of by-products. The yield is 95%.

What is claimed is:

1. A process for the preparation of a nitrodiphenyl disulfide of the formula

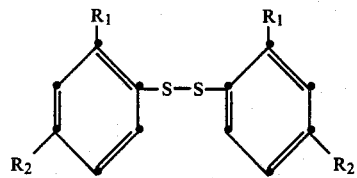

by reacting a halonitrobenzene of the formula

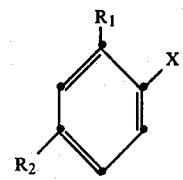

in which formulae above X is chlorine, bromine or iodine, $R_1$ is hydrogen or nitro and $R_2$ is hydrogen, $C_1$-$C_4$ alkyl, halogen, nitro or sulfo, with the proviso that at least one of $R_1$ and $R_2$ is nitro, with an alkali disulfide, which process comprises carrying out the reaction in water with the addition of 2 to 30% by weight, based on halonitrobenzene, of a non-ionic surfactant selected from the group of adducts of ethylene oxide and alkylphenols, fatty alcohols, fatty amines or fatty acids, the molecular weight of these adducts being in the range from 300 to 10,000, or an anionic surfactant selected from the group of condensates of formaldehyde and aromatic sulfonic acids, alkylbenzimidazoledisulfonic acids containing 10 to 25 carbon atoms in the alkyl moiety, alkylphenol polyglycol ether sulfates or phosphates containing 5 to 15 carbon atoms in the alkyl moiety, fatty alcohol glycol ether sulfates, sulfonated or sulfated dicarboxylic acid esters or $C_6$-$C_{20}$-alkylbenzenesulfonates.

2. A process according to claim 1, wherein the surfactant is a non-ionic surfactant.

3. A process according to claim 1, wherein the surfactant is an adduct of a saturated or unsaturated $C_{14}$-$C_{20}$fatty acid and 5 to 40 moles of ethylene oxide based on 1 mole of fatty acid, alone or in admixture with a $C_6$-$C_{20}$alkylbenzenesulfonate.

4. A process according to claim 1, wherein the surfactant is a $C_4$-$C_{12}$alkylphenol ethoxylate which is unesterified or esterified with phosphoric acid.

5. A process according to claim 1, wherein the surfactant is used in an amount of 5 to 10% by weight, based on halonitrobenzene.

6. A process according to claim 1, wherein at the start of the reaction the amount of water is 40 to 70% by weight, based on halonitrobenzene.

7. A process according to claim 1, wherein the reaction is carried out in the temperature range from 40° to 100° C.

8. A process according to claim 1, wherein the starting compound and the disulfide formed during the reaction are dispersed in the reaction medium.

9. A process according to claim 1, wherein the halonitrobenzene, water and the surfactant are charged to the reactor and the alkalidisulfide is added in the form of an aqueous solution.

10. A process according to claim 1, wherein the starting material is 1-chloro-2-nitrobenzene.

* * * * *